(12) United States Patent
Dunn

(10) Patent No.: US 10,759,128 B2
(45) Date of Patent: Sep. 1, 2020

(54) HASHISH CIGARETTE PRODUCT AND METHOD OF MANUFACTURE

(71) Applicant: Squishy Scientific, LLC, Portland, OR (US)

(72) Inventor: Adam Dunn, Portland, OR (US)

(73) Assignee: Squishy Scientific, LLC, Portland, OR (US)

( * ) Notice: Subject to any disclaimer, the term of this patent is extended or adjusted under 35 U.S.C. 154(b) by 267 days.

(21) Appl. No.: 15/727,509

(22) Filed: Oct. 6, 2017

(65) Prior Publication Data

US 2019/0105859 A1 Apr. 11, 2019

(51) Int. Cl.
| | |
|---|---|
| *B29D 23/00* | (2006.01) |
| *A61K 9/70* | (2006.01) |
| *B29C 43/00* | (2006.01) |
| *A24C 5/46* | (2006.01) |
| *A61K 36/18* | (2006.01) |
| *A61K 36/185* | (2006.01) |

(52) U.S. Cl.
CPC ............... *B29D 23/00* (2013.01); *A24C 5/46* (2013.01); *A61K 9/7007* (2013.01); *A61K 36/18* (2013.01); *A61K 36/185* (2013.01); *B29C 43/006* (2013.01); *B29K 2093/00* (2013.01)

(58) Field of Classification Search
CPC .................................. D29D 23/00; A24C 5/46
USPC ....................................................... 131/359
See application file for complete search history.

(56) References Cited

U.S. PATENT DOCUMENTS

| | | | | |
|---|---|---|---|---|
| 7,377,281 | B2 * | 5/2008 | Bachmann | A24C 5/46 |
| | | | | 131/347 |
| 9,044,390 | B1 * | 6/2015 | Speier | A61K 36/00 |
| 10,463,068 | B2 * | 11/2019 | Soo | A24B 3/14 |
| 2017/0112188 | A1 * | 4/2017 | Ostrander | A24D 1/025 |
| 2017/0188623 | A1 * | 7/2017 | Cranford | A24C 5/06 |

OTHER PUBLICATIONS

Dry Sieved Hashish, Philosopher Seeds, https://www.philosopherseeds.com/blog/en/dry-sieved-hashish/ (Year: 2016).*
DrySift Screen Materials, The Marijuana Source, https://www.rollitup.org/t/dry-sift-screen-materials.938041/ (Year: 2017).*
Screen Captures from YouTube Video Entitled "Home Video Jack Puck," 6 pages, uploaded by user videotubej3b, https://www.youtube.com/watch?v=hzPDuEoN30Q (Year: 2009).*

* cited by examiner

*Primary Examiner* — Eric Yaary
*Assistant Examiner* — Russell E Sparks
(74) *Attorney, Agent, or Firm* — Elliott, Ostrander & Preston, P.C.

(57) ABSTRACT

A fully formed, freestanding, curvilinear geometric shaped, hashish cigarette product. A method of making the product consisting, substantially of hashish, the method comprising applying pressure to a collection of kief via a press for a period of time sufficient to form a pliable sheet of hashish having a thickness of 0.5 to 1 mm, cutting or trimming the pliable sheet into a substantially rectangular section, rolling the section of pliable sheet around an object having a curvilinear geometric shape at least one full rotation, and separating the rolled section of pliable sheet from the object, leaving only the fully formed, freestanding, curvilinear geometric shaped, hashish cigarette product.

3 Claims, 4 Drawing Sheets

HASHISH CIGARETTE PRODUCT AND METHOD OF MANUFACTURE

TECHNICAL FIELD

Embodiments of the invention relate to a *cannabis* product and method of making the same. In particular, embodiments relate to a curvilinear geometric shaped, e.g., circular shaped, freestanding, hashish cigarette product consisting substantially of hashish, and method of making the same.

BACKGROUND

Kief, sometimes transliterated as keef or kif, refers to the resinous trichomes of *cannabis* that may accumulate in containers or be sifted from loose, dried or cured *cannabis* flower with a mesh screen or sieve. The kief may be pressed into a "brick" of hashish, or, simply, "hash". A portion of the hash, or the kief itself, may be gathered and wrapped in a cigarette paper to maintain its form in the shape of a cigarette. This requires a person to obtain kief, a container of some sort in which to store it, and cigarette papers. One must then take some hash, a cigarette paper, and roll a cigarette therewith for consumption. What is needed is a fully formed, freestanding, hashish cigarette that is easy to store and consume, without the need to maintain a store of kief and cigarette papers, or to roll a hash cigarette.

BRIEF DESCRIPTION OF THE DRAWINGS

Embodiments are illustrated by way of example, and not by way of limitation, and can be more fully understood with reference to the following detailed description when considered in connection with the figures in which.

DETAILED DESCRIPTION

Figure 1:
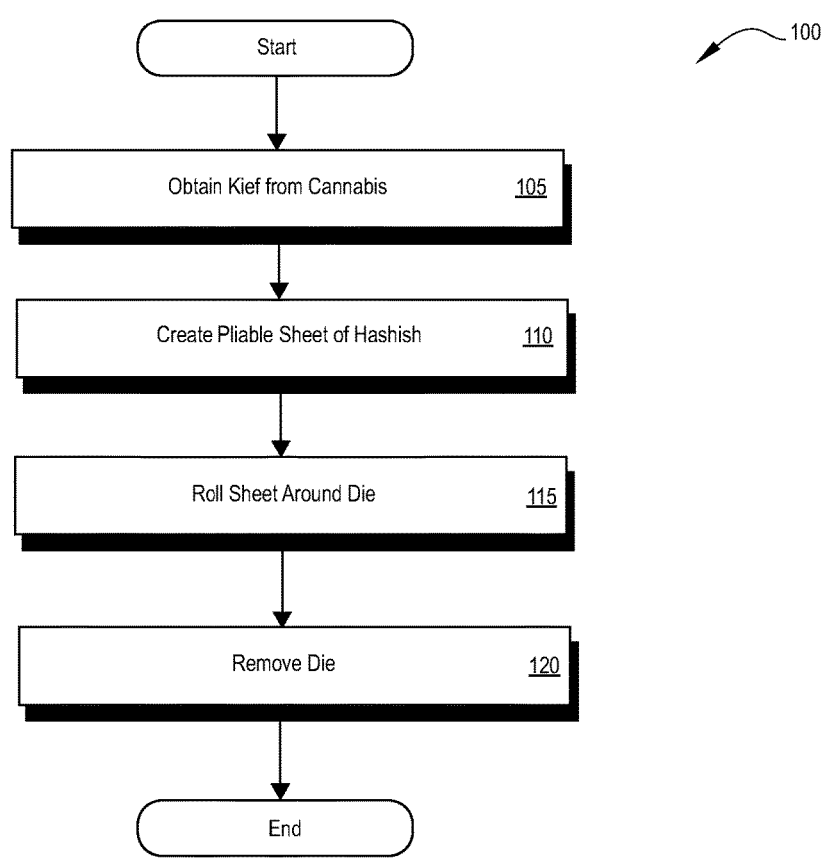
FIG. 1 illustrates an embodiment of the invention.
Figure 2:
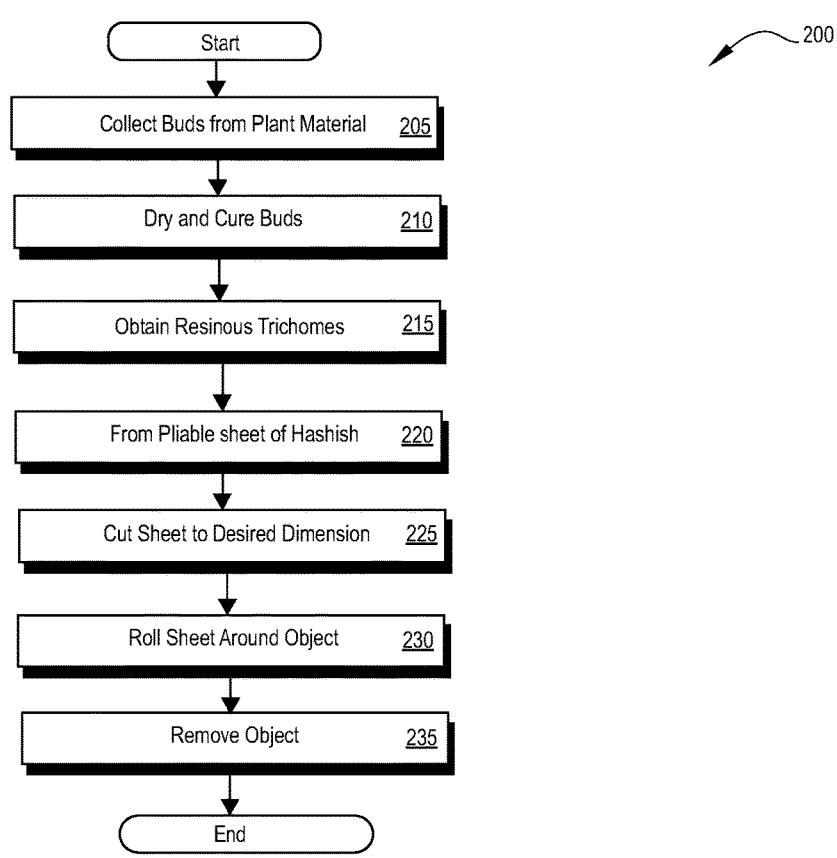
FIG. 2 illustrates an embodiment of the invention.

Embodiments of the present invention relate to a product and method of making a curvilinear geometric shaped, rigid, or freestanding, hashish cigarette product consisting substantially of hashish. With reference to FIG. 1, in one embodiment 100, the method comprises mechanically separating resinous trichomes from cured *cannabis* plant material at 105, resulting in a collection of so-called "kief" therefrom. Pressure is then applied to the kief for a period of time sufficient to form a pliable sheet of hashish, at 110. At 115, the pliable sheet of hashish is then rolled at least one full rotation around the circumference of an object having a curvilinear geometric shape, for example, a circular metal die. The object around which the pliable sheet of hashish is rolled is then removed at 120, leaving only a fully formed, rigid, or freestanding, curvilinear geometric shaped, hashish cigarette product. In one embodiment, heat may be applied to the kief during at least a portion of the time sufficient to form the sheet of hashish. It is understood that in so doing, less time is needed to form the sheet of hashish. Further details of the product and method of manufacture of the product follow.

Embodiments of the invention utilize one or more of various strains of *cannabis*, including strains of *sativa*, *indica*, or hybrids or combinations thereof, as the raw material for the freestanding hashish cigarette product. One embodiment involves separating or collecting the buds from *cannabis* plant material at 205, and drying and curing the buds at 210. Drying typically takes about 1-2 weeks, using conventional methods. Curing typically takes about 2-6 weeks, using conventional methods. The drying of the patent material generally results in an overall drying of the plant material, but yields uneven moisture and an incomplete, or unripe, terpene profile throughout the dried material, so the dried material is then cured. (Terpenes are a well-known class of organic compounds, and a primary component or constituent of essential oils found in hashish). Curing creates a more homogeneous product in terms of moisture and content. In one embodiment, curing is completed when moisture content drops below a threshold of, for example, 15% water content. In an alternative embodiment, the dried plant material may be freeze-dried rather than cured. Freeze drying typically takes 24 hours, which is far less time than the month or so of time it takes to cure the buds to yield the correct or desired balance of essential oils in the buds of the *cannabis* plant.

Figure 3:
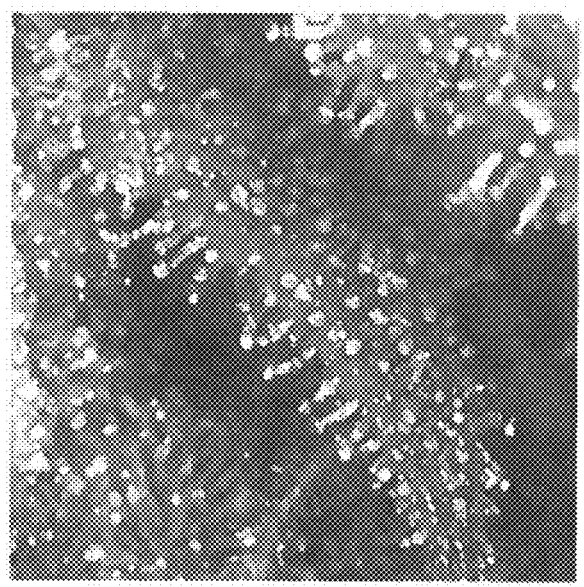
FIG. 3 is a picture of trichomes as may be harvested in accordance with an embodiment of the invention.
Figure 4:
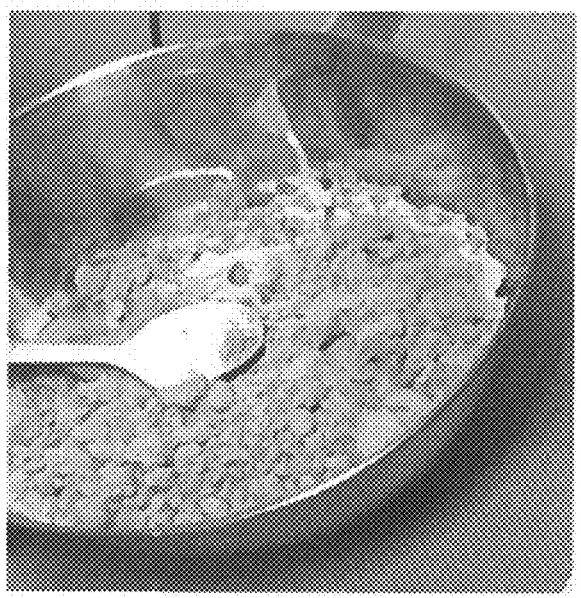
FIG. 4 is a picture of kief as used in an embodiment of the invention.

In one embodiment, resinous trichomes, visible as little crystals that cover the leaves and buds of a *cannabis* plant, are obtained at 215 using a technique in which the crystals are separated from the cured *cannabis* plant material. In one embodiment, the resinous trichomes are mechanically separated from the plant materials, such as by sieving through a screen by hand, in a motorized tumbler, an herb grinder, or a circular vibrating sifting machine. This technique is known as "drysifting", and the resulting collection of crystals is known as "drysift" or "kief", a picture of which is provided in FIG. 4. In one embodiment, a 125-165 micron mesh screen is used to obtain the trichomes (shown in the picture in FIG. 3). In particular, in one embodiment, a suitably sized micron mesh screen is used to obtain the primarily smaller, bulbous trichomes and capitate sessile trichomes, as compared to the larger, capitate-stalked trichomes, the latter of which are 50-100 mm wide. In other embodiments, the mesh screen may be in the range of 50 microns to 200 microns.

In one embodiment, a tumbler, such as a tumbler manufactured by Pollen Masters, of Los Angeles, Calif., is used to mechanically separate the resinous trichomes from the buds. The tumbler may be operated for a period of 20 minutes in one embodiment. In another embodiment, the time period may be greater than 20 minutes, for example, up to 1 hour, depending on the desired quality/purity of the end product in terms of terpene content, wherein the longer period of sifting time, the lower the quality/purity of the end product owing to other parts of the plant sifting through and being included in the kief or drysift powder that is collected in the process.

At 220, the process continues with applying pressure to the kief for a period of time. In one embodiment, the period of time is 1 minute. In another embodiment, the time under pressure may be in the range of 20-100 seconds, depending on the temperature and pressure being applied to the kief. In one embodiment the pressure applied is measured at 120 PSI. In another embodiment, the pressure may range from 20-150 PSI depending on the length of time pressure is applied and the ambient temperature during at least a portion of the time pressure is applied. Various means may be used to apply pressure to the kief, such as a roller press, pneumatic press, hydraulic press, or the like. In one embodiment, a 10"×3" heated plate press available from PurePressure, of Denver, Colo., is used to apply pressure to the kief. Applying pressure to the kief results in a pliable or flexible sheet of hashish. In one embodiment, the sheet has a thickness of 0.5-1 mm.

In one embodiment, temperature is controlled during at least a portion of the time the kief is under pressure. According to one embodiment, temperature is maintained at 130 degrees Fahrenheit for some or all of the time the kief is under pressure. In another embodiment, temperature may be controlled in a range from 90-200 degrees Fahrenheit. It is understood that the more pressure being applied, and/or the longer the period of time pressure is applied, the less heat that is needed and/or the shorter the period of time that is needed to apply heat. It is understood that better terpene preservation in the hashish sheet is accomplished by applying pressure while at lower temperatures.

Figure 5:
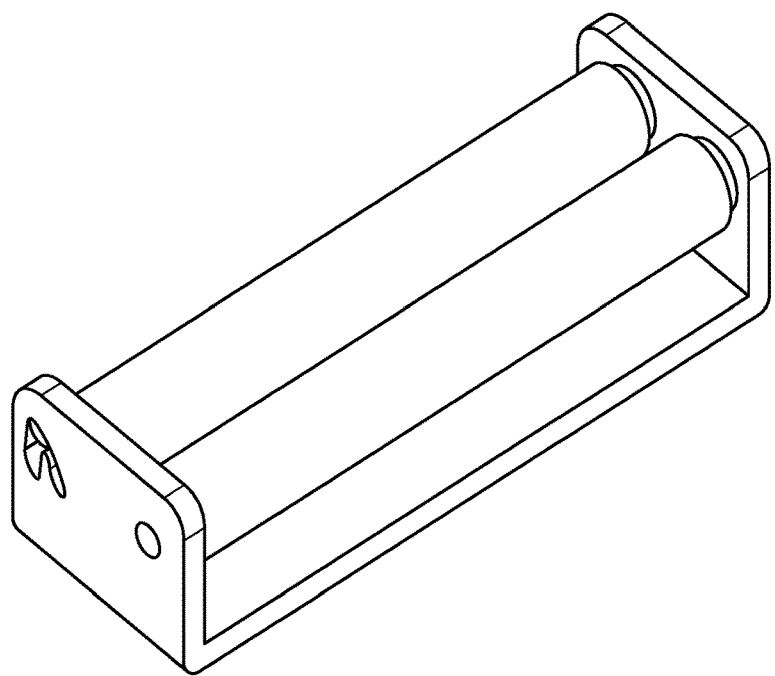
FIG. 5 is a picture of a cigarette roller as may be used in an embodiment of the invention.
Figure 6:
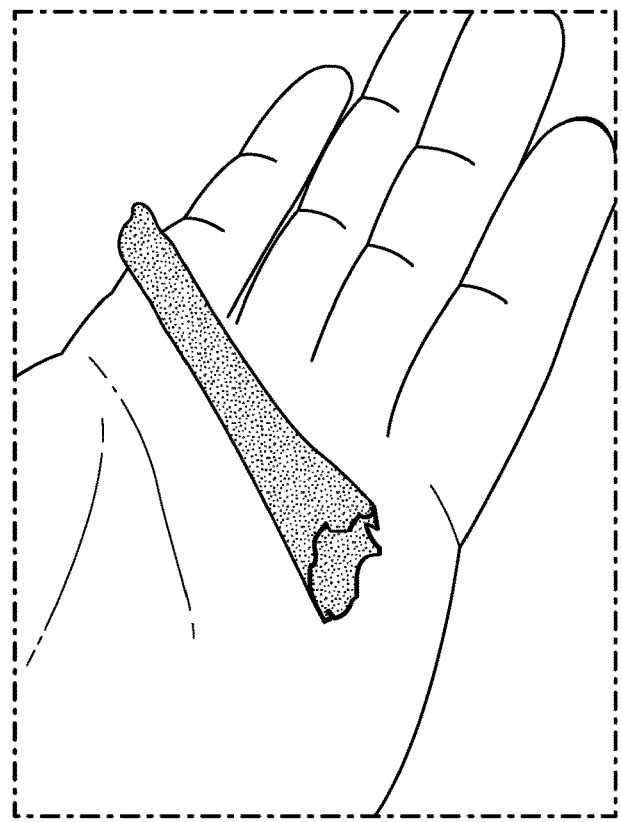
FIG. 6 is a picture of a fully formed, freestanding, curvilinear geometric shaped, hashish cigarette product, according to an embodiment of the invention.

The sheet, once formed, may be trimmed and or cut at 225 to desired dimensions of width and length. For example, depending on the size of the object or roller around which the sheet is to be rolled or otherwise formed, the sheet is cut to size accordingly. For example, if a roller such as depicted in FIG. 5 is used to roll the sheet into a tube shape, the sheet is cut to a length not exceeding the length of the roller, and to a width at least equal to the circumference of the roller, as needed, so that a fully formed tube may be created by rolling the sheet through the roller. Alternatively, the sheet may be rolled first around the object at 230, as further described below, the object and sheet then separated from one another, and then the freestanding product, pictured in FIG. 6, may be trimmed or cut to a desired length, or not at all.

In one embodiment, the sheet of hashish is rolled or otherwise formed around an object generally having a curvilinear geometric shape, such as a cigarette roller or metal die in the shape of a cylinder (see FIG. 5). In one embodiment, the roller or die has a diameter of 5-7 mm and a length along its longitudinal axis of 70-110 mm. In one embodiment, the diameter of the object may be consistent along its length. In another embodiment, the diameter of the object may vary along its length, for example, in the shape of a cone that tapers linearly, or nonlinearly, from a flat base having a diameter of 5-7 mm to an apex or vertex having a smaller diameter that provides an opening allowing for air to flow through the resulting cone shape of the finished product.

Once the sheet of hashish is rolled or formed in to a desired shape, the object is removed at 235, and/or the shaped hashish sheet is separated from the object, resulting in fully formed, rigid or free-standing, curvilinear geometric shaped, hashish cigarette product.

The freestanding hashish cigarette product manufactured as described above is stable and maintains its shape without further treatment of manufacturing processes. Optionally, the cigarette may be wrapped in paper, e.g., cigarette paper to better protect and maintain its shape. In another optional embodiment, a food grade adhesive (e.g., a marijuana extract or rosin) may be placed on the inside of an outer layer that overlaps an inner layer of the rolled hashish cigarette. The adhesive glues or otherwise holds the outer layer to the inner layer and thus better maintains the cigarette's shape. The adhesive may be applied either before or after rolling the sheet. In yet another optional embodiment, the food grade adhesive is applied to the opposing edges of the sheet so that when the opposing edges of the sheet are brought together upon rolling the sheet in a circumference around the object, the opposing edges adhere to one another and thus better maintain the cigarette's shape.

Once the hashish cigarette is formed, it is preferable to store it in a cool, dry, dark place, to better preserve its shape and terpene content. Optionally, materials may be inserted into the hollow tube portion of the cigarette, e.g., marijuana, hashish, tobacco, herbs or other plant material, optionally infused with essential oils, may be inserted into the hollow portion of the hashish cigarette.

Although the invention has been described and illustrated in the foregoing illustrative embodiments, it is understood that the present disclosure has been made only by way of example, and that numerous changes in the details of implementation of the invention can be made without departing from the spirit and scope of the invention, which is only limited by the claims that follow. Features of the disclosed embodiments can be combined and rearranged in various ways.

What is claimed is:

1. A method of making a freestanding hashish cigarette product, comprising:
    collecting material from a cannabis plant;
    drying and curing the collected material to a moisture content not exceeding 15%;
    mechanically separating resinous trichomes from the dried and cured collected material using a 125 to 165 micron mesh screen for a period of approximately 20 minutes, resulting in collection of kief;
    applying pressure of 120 PSI to the collection of kief for a period of approximately 1 min using a temperature controlled plate press, resulting in a pliable sheet of hashish having a thickness of 0.5-1 mm;
    rolling the pliable sheet of hashish around an object having a curvilinear geometric shape; and
    removing the object, resulting in fully formed, freestanding, curvilinear geometric shaped, hashish cigarette.

2. The method of claim 1, wherein the object having a curvilinear geometric shape is a metal die in the shape of a cylinder, with a diameter in a range of 5-7 mm and having a longitudinal axis in a range of 70-110 mm.

3. The method of claim 1, wherein applying pressure of 120 PSI to the collection of kief for a period of approximately 1 minute using a temperature controlled plate press comprises applying such pressure for the defined period using a temperature controlled plate press wherein the temperature is controlled to not exceed 130 degrees Fahrenheit.

* * * * *